US006641781B2

(12) United States Patent
Walta (10) Patent No.: US 6,641,781 B2
(45) Date of Patent: Nov. 4, 2003

(54) SYSTEM FOR CLEANING, DISINFECTING AND/OR DRYING ENDOSCROPES

(76) Inventor: Johannes Antonius Walta, Meidoornlaan 5, 2267 BA Leidschendam (NL)

( * ) Notice: Subject to any disclaimer, the term of this patent is extended or adjusted under 35 U.S.C. 154(b) by 0 days.

(21) Appl. No.: 09/397,828

(22) Filed: Sep. 17, 1999

(65) Prior Publication Data

US 2002/0146344 A1 Oct. 10, 2002

(30) Foreign Application Priority Data

Sep. 18, 1998 (NL) .............................. 1010130

(51) Int. Cl.[7] .............................. A61L 9/00; B01J 19/00; B08B 9/20; B08B 3/00; E04H 15/12
(52) U.S. Cl. .............................. 422/28; 422/32; 422/40; 134/254; 134/26; 134/61; 134/92; 134/88
(58) Field of Search .......................... 422/28, 40, 292, 422/295, 297, 300, 301; 134/88–90, 26, 92, 61, 25.4

(56) References Cited

U.S. PATENT DOCUMENTS

| | | | |
|---|---|---|---|
| 4,262,800 A | | 4/1981 | Nethercutt |
| 4,915,913 A | | 4/1990 | Williams et al. |
| 5,225,160 A | * | 7/1993 | Sanford et al. ............... 422/28 |
| 5,279,799 A | * | 1/1994 | Moser ....................... 422/292 |
| 5,288,467 A | * | 2/1994 | Biermaier .................... 422/116 |
| 5,425,815 A | * | 6/1995 | Parker et al. .................. 134/26 |
| 5,738,824 A | * | 4/1998 | Pfeifer .......................... 422/3 |

FOREIGN PATENT DOCUMENTS

DE          29 31 366          2/1981

* cited by examiner

Primary Examiner—Robert J. Warden, Sr.
Assistant Examiner—Monzer R. Chorbaji
(74) Attorney, Agent, or Firm—Katten Muchin Zavis Rosenman (57) ABSTRACT

During the treatment, in particular cleaning, disinfecting and drying, of used, dirty endoscopes, in order to render them suitable once again for subsequent use, the following steps take place: placing a used, dirty endoscope in a rack, connecting the passages of the endoscope to a connection block which is arranged in a fixed position in the rack, placing the rack, with the endoscope therein, in at least one device for treating the endoscope, the connection block being connected to a counter-connection block which is present in the treatment device, in order to bring about a connection between the endoscopes and the treatment device, subjecting the endoscope which is accommodated in the rack to a specific treatment in the treatment device, taking the rack with the endoscope therein out of the treatment device, and uncoupling the endoscope from the connection block after it has been taken out of the final treatment device. This makes it possible to work in extremely hygienic conditions and minimizes the risk of damage to the endoscope.

2 Claims, 6 Drawing Sheets

SYSTEM FOR CLEANING, DISINFECTING AND/OR DRYING ENDOSCROPES

The invention relates to a method and system for treating, in particular cleaning, disinfecting and/or drying, used, dirty endoscopes, in order to render them suitable once again for subsequent use.

Currently, it is obligatory, between each endoscopic examination, for the endoscope to be thoroughly cleaned and disinfected. This work is usually carried out outside the room in which the examination takes place. In the process, the endoscope undergoes various treatments and movements. In general, the endoscope follows the following route. After the endoscopic examination in the examination room, the endoscope is transported to a room where the domestic cleaning, disinfecting and drying of the endoscope takes place. If appropriate, the dried endoscope is stored in this room. The endoscope is transported between each treatment. When the endoscope is to be used again, it is transported back to the examination room. It should be noted that the domestic cleaning and drying of the endoscope is sometimes omitted, depending on local regulations and conditions.

Various complications may arise in the process described above. Owing to its shape, the endoscope is not easy to handle during the operations which are to be carried out in the abovementioned process. The endoscope can easily be damaged by impacts, leading to expensive repairs. When the endoscope is picked up and moved after disinfection, the endoscope may easily become unsterile. Furthermore, there is a risk of the "dirty" endoscope unintentionally coming into contact with the environment, with the result that certain locations may be contaminated.

The object of the present invention is to overcome the drawbacks mentioned above and to provide a method and system for treating, in particular cleaning, disinfecting and/or drying endoscopes, with which it is possible to work under very hygienic conditions and the risk of damage to the endoscope is minimized.

This object is achieved by means of a method for treating used, dirty endoscopes, in order to render them suitable once again for subsequent use, comprising at least the following steps:

a) placing a used, dirty endoscope in a rack,
b) connecting the passages of the endoscope to a connection block which is arranged in a fixed position in the rack,
c) placing the rack, with the endoscope therein, in at least one device for treating the endoscope, the connection block being connected to a counter-connection block which is present in the treatment device, in order to bring about a connection between the endoscopes and the treatment device,
d) subjecting the endoscope which is accommodated in the rack to a specific treatment in the treatment device,
e) taking the rack with the endoscope therein out of the treatment device, and
f) uncoupling the endoscope from the connection block after it has been taken out of the final treatment device.

This object is also achieved by means of a system for treating used, dirty endoscopes, in order to render them suitable once again for subsequent use, comprising:

at least one rack in which an endoscope can be accommodated, the rack being provided with a fixed connection block to which the passages of an endoscope which is accommodated in the rack can be connected,
one or more treatment devices in which an endoscope which is accommodated in a rack can be subjected to a specific treatment, the treatment device being provided with a counter-connection block which can be connected to the connection block which is arranged in the rack,
an essentially identical connection block being arranged in each rack, and an essentially identical counter-connection block, which can be connected to the connection blocks arranged in the racks, being arranged in each treatment device.

The invention furthermore relates to a rack for accommodating an endoscope, which rack is provided with a connection block which is arranged in a fixed position in the rack and to which the passages of an endoscope accommodated in the rack can be connected.

The invention will be explained in more detail in the following description of a preferred embodiment with reference to the drawings, in which.

Figure 1:
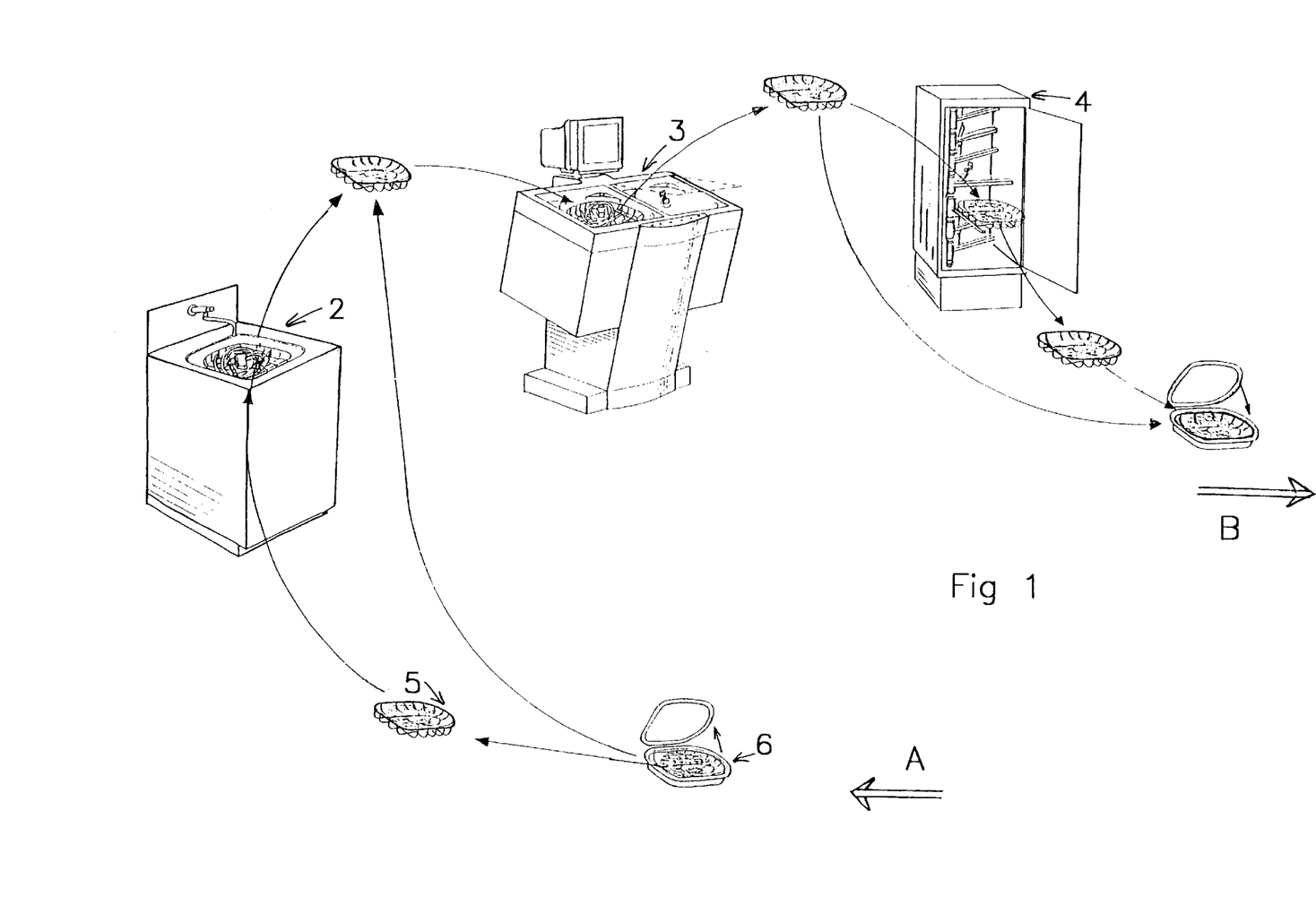
FIG. 1 diagrammatically depicts the system according to the invention for treating, in particular cleaning, disinfecting and drying, used, dirty endoscopes.

FIG. 1 diagrammatically depicts a system for treating, in particular cleaning, disinfecting and drying, used, dirty endoscopes. This system is intended to render dirty endoscopes suitable once again for subsequent use.

The system comprises a cleaning device 2 for domestic cleaning (washing) of endoscopes, a disinfecting device 3 for disinfecting endoscopes, and a drying device 4 for drying endoscopes.

Figure 5:
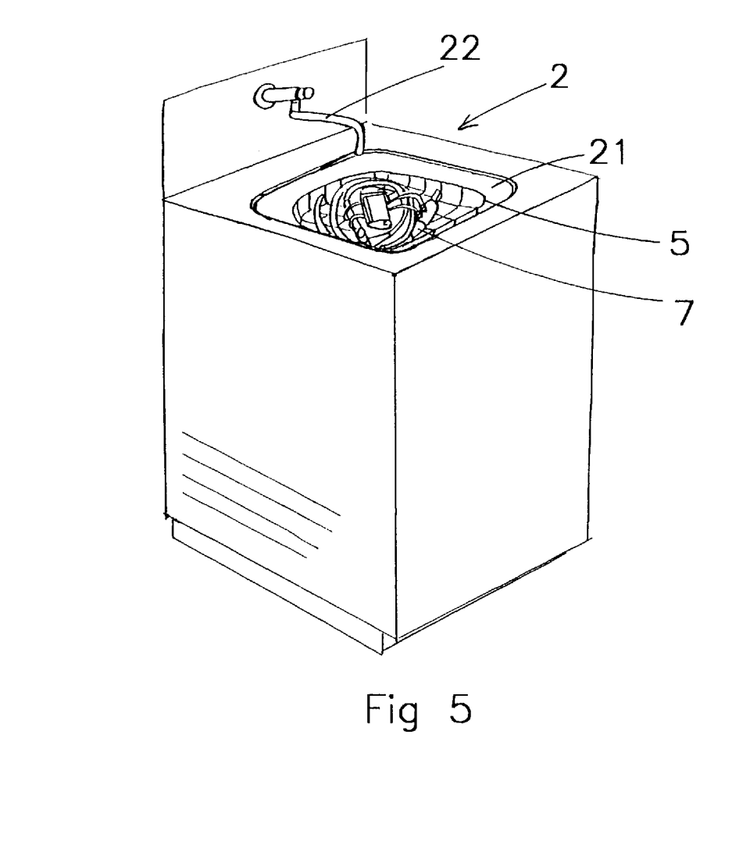
FIG. 5 shows a larger view of the device for cleaning an endoscope as shown in FIG. 1.
Figure 6:
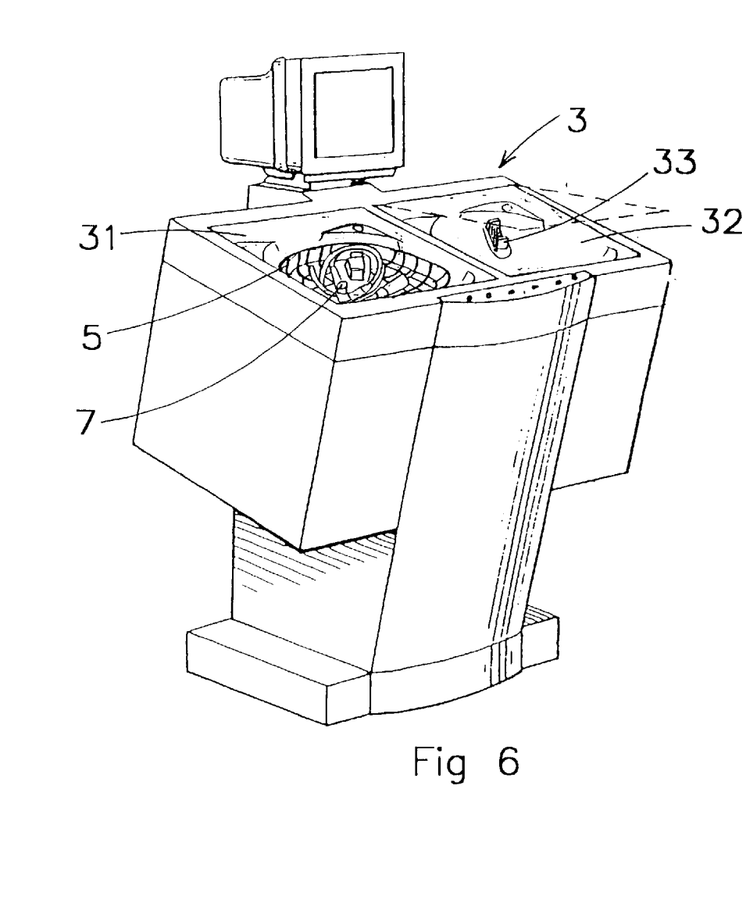
FIG. 6 shows an enlarged view of the device for disinfecting an endoscope as shown in FIG. 1.
Figure 7:
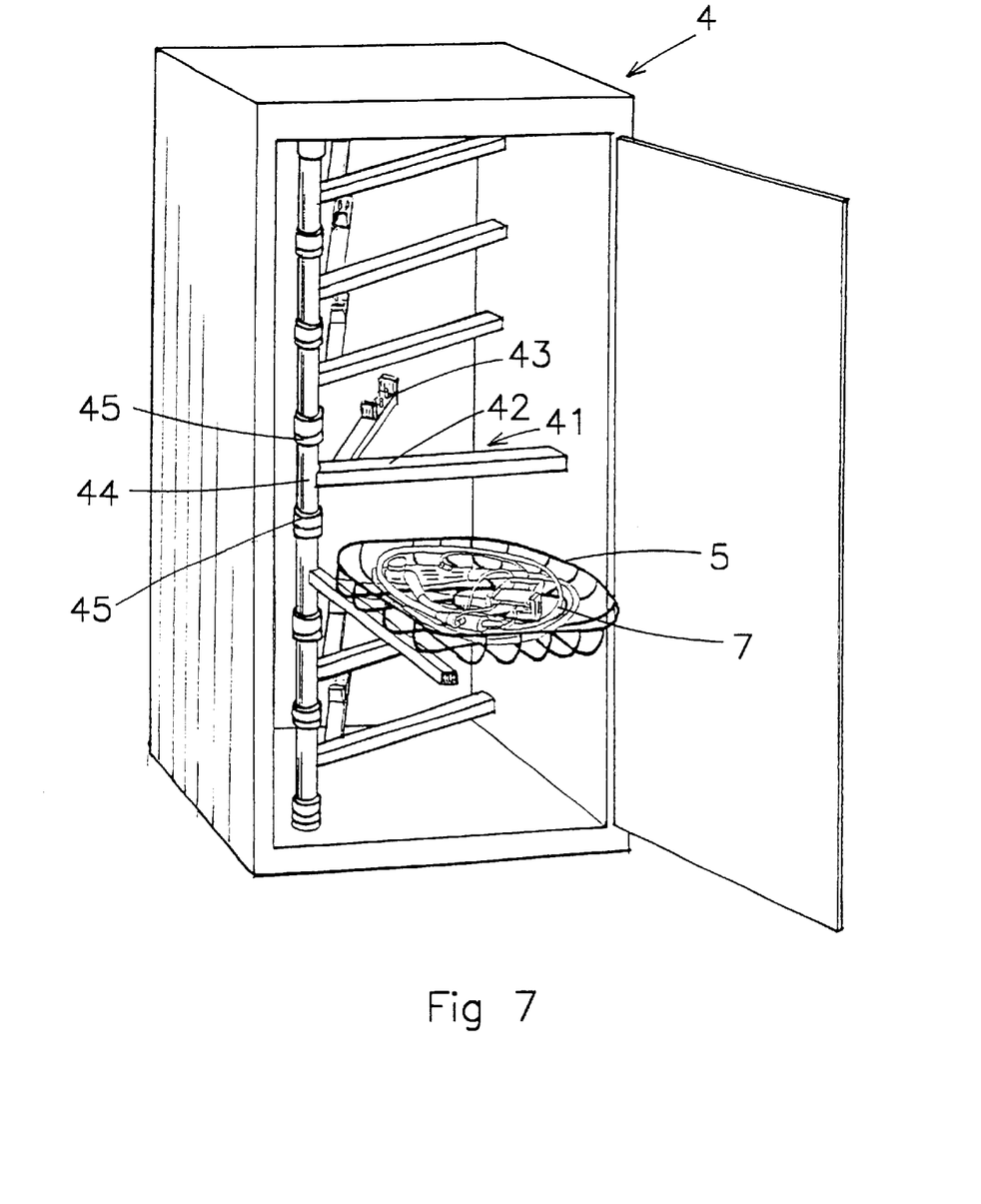
FIG. 7 shows an enlarged view of the device for drying an endoscope as shown in FIG. 1.

The cleaning device 2, the disinfecting device 3 and the drying device 4 are shown on a larger scale in FIGS. 5, 6 and 7, respectively.

Figure 2:
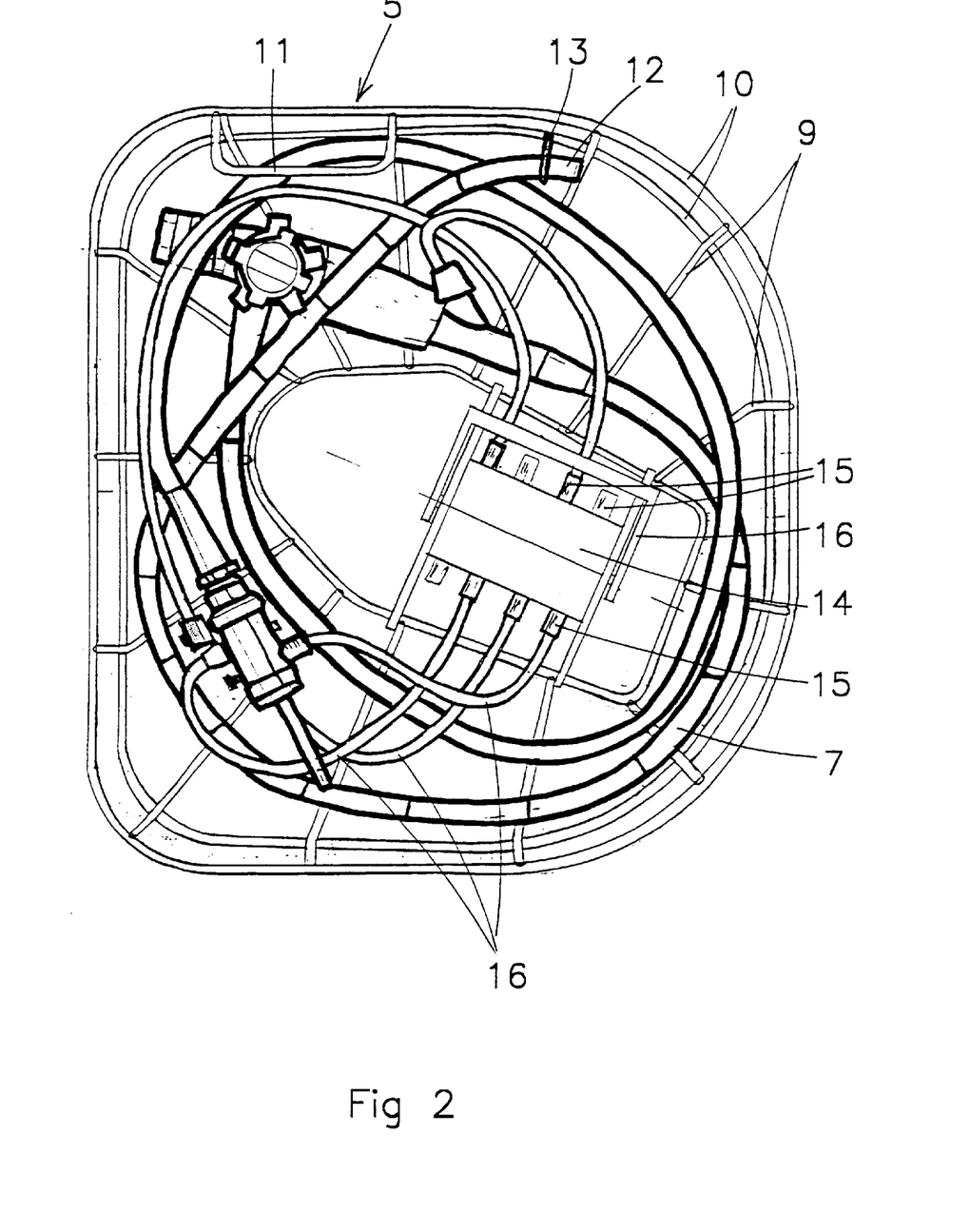
FIG. 2 shows a plan view of a rack according to the invention, with an endoscope therein.
Figure 3:
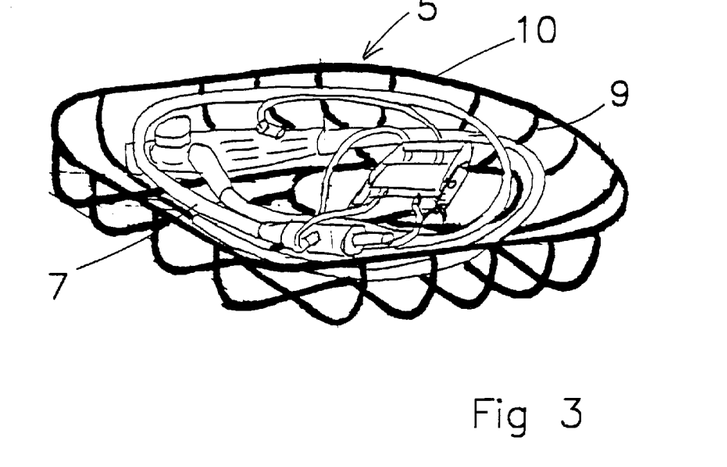
FIG. 3 shows the rack, with the endoscope therein, of FIG. 2, on a somewhat smaller scale and as a perspective view.
Figure 4:
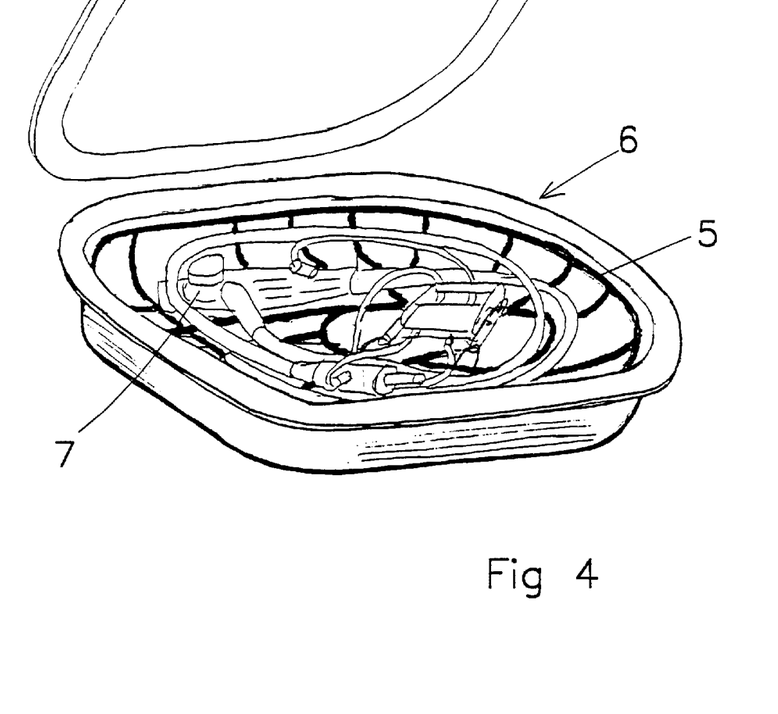
FIG. 4 shows the rack, with the endoscope therein, shown in FIG. 3, accommodated in a closable carrier tray.

The system furthermore comprises at least one rack 5, in which an endoscope can be accommodated, and at least one closable carrier tray 6, in which a rack 5, with an endoscope therein, can be placed. FIGS. 2 and 3 show a rack 5 of this nature with an endoscope 7 therein. FIG. 4 shows a carrier tray 6 holding a rack 5 with endoscope 7. The carrier tray 6 can be closed off by means of a lid 8.

The rack 5 (cf. FIGS. 2 and 3) is formed from bended rods 9 and 10 which are fixedly connected to one another. The rack 5 is provided with one or two handles 11, by means of which the rack can be gripped and lifted up. The rack 5 is furthermore formed in such a manner that an endoscope 7 can be placed therein in a more or less folded state. In order to be able to fix in particular the fragile end 12 of the endoscope, the rack is provided with a tip holder 13.

A connection block 14 is arranged fixedly in the rack. This connection block is provided with passages and ports 15 which are connected to the passages and can be connected to the passages of the endoscope 7 by means of flexible tubes 16. On its underside (not visible in FIG. 2), the connection block 14 is provided with connection points for the connection of counter-connection blocks, which are to be described in more detail below. The connection block 14 is furthermore provided with a handle 16a. By moving the handle 16a, the connection block 14 can be connected to a counter-connection block or removed therefrom.

The cleaning device 2 (FIG. 5) for the domestic cleaning (washing) of an endoscope is a conventional device, generally with a standard rinsing tray 21. In the rinsing tray 21, there is a counter-connection block, which can be connected to the connection block 14 and is connected to the water supply 22 via the underside of the rinsing tray 21. A rack 5, with an endoscope 7 therein, can be placed in the rinsing tray 21, the connection block 14 being connected to the counter-connection block which is present in the rinsing tray. In the cleaning device 2, an endoscope can be domestically cleaned, and the passages of the endoscope can be rinsed with water.

The disinfecting device 3 (FIG. 6) is, for example, a cleaning device as described in EP-A-0 709 056, the contents of which is included herein by reference. This disinfecting device 3 is provided with two trays 31 and 32 in which a rack 5, with an endoscope 7 therein, can be accommodated. In FIG. 6, a rack of this nature is located in the left-hand tray. Both trays 31 and 32 are provided with a counter-connection block which, when a rack 5 is placed in the tray 31, 32, can be connected to the connection block 14 arranged in the rack 5. The counter-connection block arranged in the right-hand tray can be seen in FIG. 6 and is denoted by the reference numeral 33. In the disinfecting device 3, an endoscope can be disinfected in the manner described in EP-A-0 709 056.

The drying device 4 (FIG. 7) is designed as a drying cabinet containing a number of holders 41 which are located one above the other and are each designed to accommodate a rack 5 with an endoscope 7 therein. Each holder 41 comprises a two-limbed carrier arm, on which a counter-connection block 43, which can be connected to a connection block 14 arranged in the rack 5, is arranged. One end of the carrier arm 42 is attached to a round pipe part 44. At least that limb on which the counter-connection block 43 is arranged is already in place and, via a connection passage, is in communication with the interior of the pipe part. The pipe part 44 is pushed over a round, hollow post (not visible). At its ends, the pipe part 44 is provided with a bearing and an air seal 45. A hole is arranged in the hollow post, at the level of the connection between the hollow limb of the holder 41 and the interior of the pipe part 44. By placing the inside of the post under (air) pressure and aligning the holes in the post with the connecting passage to the hollow limb of the carrier arm 41, air can be guided via the pipe part and carrier arm 41, to the counter-connection block 43. When a rack 5 with an endoscope 7 therein is placed on the support arm 41, with the counter-connection block 43 connected to the connection block 14 of the rack 5, air can be blown through the endoscope 7 accommodated within the rack 5, and this endoscope can be dried internally. When the carrier arm 41 is moved into a different position, the air supply to the counter-connection block 43 is closed off. This position is used when there is no rack 5 present or, when the holder 41 has been rotated all the way outwards, in order to place a rack 5 on the holder 41.

Figure 8:
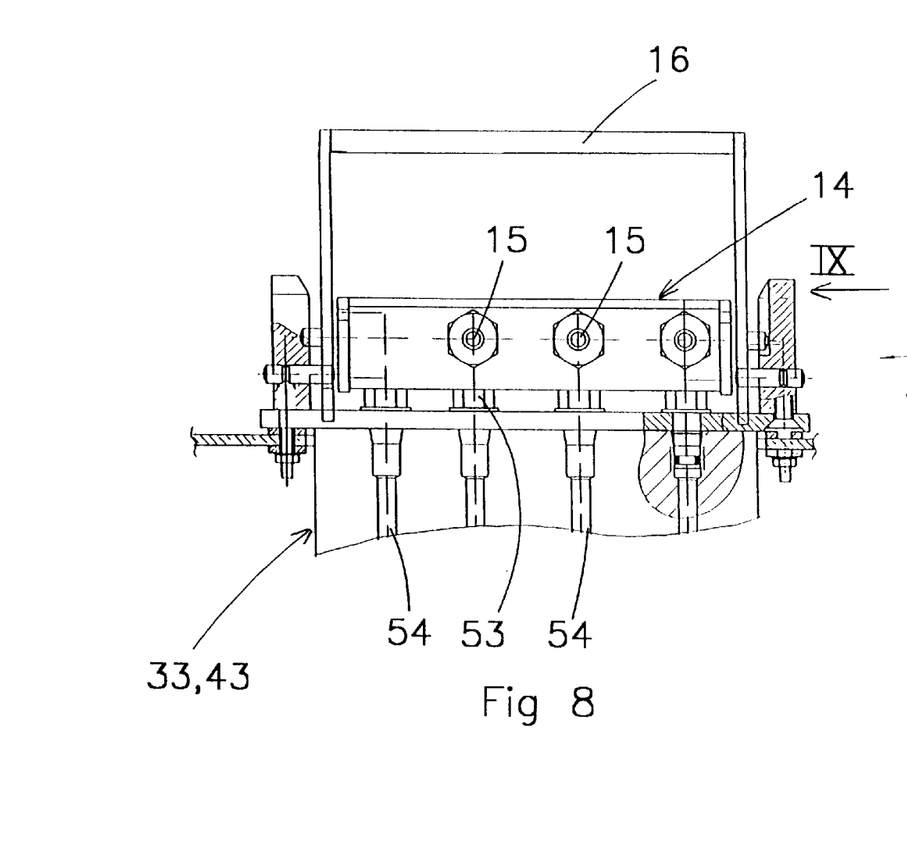
FIG. 8 shows a side view, partially in section, of the connection block arranged in the rack according to the invention and the counter-connection block arranged in a device for treating an endoscope, in the connected state.
Figure 9:
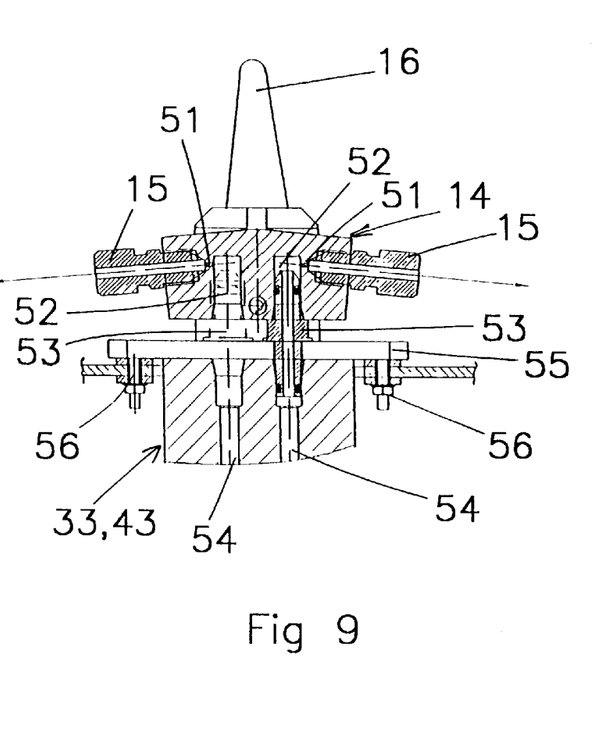
FIG. 9 shows a view, partially in section, of the connection block and the counter-connection block shown in FIG. 8, seen in the direction of arrow IX.

FIGS. 8 and 9 show a connection block 14 which is arranged in a rack 5 and a counter-connection block 33, 43 in more detail. The handle 16a of the connection block 14 is also shown. On its side, the connection block 14 is provided with ports 15 which, via passages 51 in the connection block 14, are in communication with holes 52 in the connection block 14, into which holes columns 53 of the counter-connection block 33, 43 fit. These columns 53 are in turn connected to passages 54 in the counter-connection block 33, 43.

As stated above, flexible tubes can be connected to the ports 15, which tubes, at their other end, are connected to passages in the endoscope 7. With the aid of the connection block 14 and a counter-connection block 33, 43, the passages of an endoscope 7 can be connected to the passages in the counter-connection block 33, 43.

The counter-connection block 33, 43 is provided with a carrier plate 55 which, by means of bolts 56, can be attached to a device for treating an endoscope, such as the cleaning device 2, the disinfecting device 3 and the drying device 4. In principle, the counter-connection blocks in the cleaning device 2, the disinfecting device 3 and the drying device 4 are of identical design and fit the connection block 14 of a rack 5. As a result, an endoscope 7 which is accommodated in a rack 5 can very easily be coupled to each of the said treatment devices.

The following procedure is adopted when treating, in particular cleaning, disinfecting and drying, a used, dirty endoscope.

In the examination room, the endoscope, following an endoscopic examination, is placed in a rack 5. The rack 5 is already situated in a carrier tray 6 or is placed therein. Then, the lid 8 is placed onto the carrier tray. After that, the carrier tray 6, which has been closed off by lid 8 and holds the endoscope, is moved to the treatment room (arrow A in FIG. 1). In the treatment room, the lid 8 is removed from the carrier tray 6, and the passages of the endoscope 7, with the aid of flexible tubes 16, are connected to the ports 15 of the connection block 14 arranged in the rack 5. The rack 5, with the endoscope 7 therein, is taken out of the carrier tray 6 and placed in the washing tray 21 of the cleaning device 2, the connection block 14 being coupled to the counter-connection block in the washing tray 21. The endoscope is then domestically cleaned. The carrier tray 6 and the lid 8 are disinfected separately.

After disconnection, the rack 5, with the endoscope 7 therein, is moved to the disinfecting device 3 and is placed in one of the two trays 31, 32, the connection block 14 again being connected to a counter-connection block 33. The endoscope is then disinfected in the customary way, such as as described, for example, in EP-A-0 709 056.

After disconnection, the rack 5, with endoscope therein, is moved to the drying device 4 and is placed on one of the holders 41, the connection block 14 being connected to a counter-connection block 43. Drying medium is then blown through the endoscope 7. It should be noted that in the event that the endoscope 7 has to be reused immediately, the drying of the endoscope is dispensed with.

The dried endoscope remains in the drying device 4 until the endoscope is again required for a further examination. Just before use, the endoscope 7, with rack 5, is taken out of the drying device 4 (or out of the disinfecting device 3, in the event of immediate use), and is placed in a disinfected carrier tray 6. The flexible tubes 16 are disconnected from the endoscope 7 and a disinfected lid 8 is placed on the carrier tray 6.

Then, the carrier tray 6, containing the endoscope 7 accommodated in the rack 5, is transported to the examination room (arrow B in FIG. 1). In the examination room, the lid 8 is removed from the carrier tray 6, and the endoscope 7 is taken out of the rack 5 in order to carry out an endoscopic examination.

It should be noted that in certain cases, depending on the local regulations and conditions, the domestic cleaning in the cleaning device 2 and the drying in the drying device 4 may sometimes be omitted.

As will be clear from the above text, there is no contact with the endoscope along its entire route from the examination room to the treatment room and back. Also, the endoscope does not come into contact with the environment, thus preventing damage to the endoscope and/or contamination to the environment. The transportation of the endoscope between the examination room and the treatment room and back takes place in a closed carrier tray 6.

The system according to the invention has the following advantages:

- high levels of hygiene, since the disinfected endoscope is only picked up just before the examination takes places,
- less risk of damage to the endoscope as a result of impacts and the like,
- less risk of contamination to the environment from the "dirty" endoscope,
- the endoscope is much easier to handle, due to the shape of the rack,
- universal coupling system for all treatment devices,
- during the coupling, the passages of the endoscope are automatically connected to passages in a treatment device,
- the endoscope remains in the rack during transportation, cleaning, disinfecting and drying.

Finally, it can also be pointed out that in principle each endoscope may have its own rack, the ports of the connection block in the rack being adapted to the type of endoscope which is to be accommodated in the rack.

What is claimed is:

1. A method for treating used, dirty endoscopes, in order to render them suitable once again for subsequent use, comprising at least the following steps:

a) placing a used, dirty endoscope in a rack, b) connecting the passages of the endoscope to a connection block which is arranged in a fixed position in the rack, no portion of the endoscope being within the connection block upon connection of the passages of the endoscope to the connection block, c) transporting the rack, with the endoscope therein, to one of a plurality of different treatment devices for treating the endoscope, each of said plurality of different treatment devices not having an enclosing wall in common with any other of said plurality of different treatment devices, d) placing the rack, with the endoscope therein, in said one or in said another of said plurality of different treatment devices for treating the endoscope, the connection block being connected to a counter-connection block which is present in the treatment device, in order to bring about a connection between the endoscopes and the treatment device, e) subjecting the endoscope which is accommodated in the rack to a specific treatment in the treatment device, f) taking the rack with the endoscope therein out of the treatment device, g) if the rack has not been in at least one of the plurality of different treatment devices, transporting the rack, with the endoscope therein, to another of the plurality of different treatment devices, and returning to step d), and h) uncoupling the endoscope from the connection block after it has been taken out of the final treatment device.

2. The method of claim 1, wherein the rack, with the endoscope therein, is placed in a closable carrier tray, in order for the endoscope to be transported between a room where the endoscope is used and a room where the treatment device is arranged, and vice versa, and the rack with the endoscope therein is transported in the closed carrier tray.

* * * * *

UNITED STATES PATENT AND TRADEMARK OFFICE
CERTIFICATE OF CORRECTION

PATENT NO.     : 6,641,781 B2
DATED          : November 4, 2003
INVENTOR(S)    : Walta, Johannes Antonius It is certified that error appears in the above-identified patent and that said Letters Patent is hereby corrected as shown below:

Title page,
Item [54], Title, "ENDOSCROPES" should be -- ENDOSCOPES --.

Signed and Sealed this

Tenth Day of January, 2006

JON W. DUDAS
*Director of the United States Patent and Trademark Office*